US006388055B1

(12) United States Patent
Bergsma et al.

(10) Patent No.: US 6,388,055 B1
(45) Date of Patent: *May 14, 2002

(54) MOUSE CC-CKR5 RECEPTOR POLYPEPTIDE

(75) Inventors: Derk J. Bergsma; Mary E. Brawner, both of Berwyn; Usman Shabon, Swarthmore, all of PA (US)

(73) Assignee: SmithKline Beecham Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/724,984

(22) Filed: Oct. 3, 1996

(51) Int. Cl.$^7$ .......................... C07K 14/00; C07K 17/00
(52) U.S. Cl. ......................................... 530/350; 530/351
(58) Field of Search ................................ 530/350, 351, 530/395

(56) References Cited

FOREIGN PATENT DOCUMENTS

| WO | WO96/39437 | 12/1996 |
|---|---|---|
| WO | WO 97/22698 | 6/1997 |
| WO | WO 97/32019 | 9/1997 |
| WO | WO 97/45543 | 11/1997 |
| WO | WO 97/44055 | 12/1997 |

OTHER PUBLICATIONS

Samson et al *Biochem 35*, 1996, p. 3362–67.*
Raport et al *JBC* Jul. 1996, 271, p. 171 61.*
Combadiere et al *J. Leukocyte Biol 60*, 1996, p 147.*
Ponath et al, *J. Exp Med* 183, 1996, p 2437.*
Gantz et al, *Cytogenet Cell Genet* 74, 1996, p 286–90.*
Raport et al, *J. Leukocyte Biol* 59, 1996, p 18.*
Deng, et al., "Identification of a major co–receptor for primary isolates of HIV–1", Nature, 1996, 381:661–666.
Dragic, et al., "HIV–1 entry into CD4 cells is mediated by the chemokine receptor CC–CKR–5", Nature, 1996, 381:667–673.
Ross, P. C., et al., "RTA, a candidate G protein–coupled receptor: Cloning, sequencing, and tissue distribution", Proceedings of the National Academy of Science, 1990, 87:3052–3056.
Libert, F., et al., "Selective Amplification and Cloning of Four New Members of the G Protein–Coupled Receptor Family", Science, 1989, 244:569–572.
Eva, C., et al., "Molecular cloning of a novel G protein–coupled receptor that may belong to the neuropeptide receptor family", Febs Letters, 1990, 271:81–84.
Meyer et al. "Cloning and Characterization of a Novel Murine Macrophage Inflammatory Protein–1α Receptor", J. of Biological Chemistry, 271(24):14445–14451 (1996).
Boring et al., "Molecular Cloning and functional Expression of Murine JE (Monocyte Chemoattractant Protein 1) and Murine Macrophage Inflammatory Protein 1α Receptors", J. of Biological Chemistry, 271(13):7551–7558 (1996).
Alkhatib et al., "CC CKR5: a RANTES, MIP–1α, MIP–1β Receptor as a Fusion Cofactor for Macrophage–Tropic HIV–1", Science, 272(18):1955–1958 (1996).

* cited by examiner

*Primary Examiner*—Gary L. Kunz
*Assistant Examiner*—Jegatheesan Seharaseyon
(74) *Attorney, Agent, or Firm*—William T. Han; Ratner & Prestia; William T. King

(57) ABSTRACT

Mouse CC-CKR5 polypeptides and DNA (RNA) encoding such mouse CC-CKR5 and a procedure for producing such polypeptides by recombinant techniques is disclosed. Also disclosed are methods for utilizing such mouse CC-CKR5 in the development of gene knockout mice for use as a model for human immunodeficiency virus.

2 Claims, 3 Drawing Sheets

Nucleotide and Amino Acid sequence of mouse CC-CKR5

```
        GAGAGAGAGAGAGAGAGAGaGaGaGAGAGAGAGAGAGAGAGAGaGAGAGAG  60
AGAGAGAGAGAGAGAGAGAGAGAGAGAGAGAGATCTTATTAGTTACCAAGGAGTGACA 120
AGCAACATGTCAGTTAAGGTTTCATACTGCCCAAATTCAAAGTAAGTTACTTCCTGGTGG 180
TGTGGTTTTTATATTAACATTCATTCTCTCTATACTTGGGGAGTGTTTTATCCAGAAAAA 240
CATAAACAGTATATTGCTTGCCTCAAGCAGTTAAcTCAAGTGTTTAGCAAAtGCATATGT 300
AATACTATAGAACAGTAATTAGCACCCACTACTCATTCTTTCTGGCATTTGTGTGAACTC 360
TAGGATTTATGGATAAATGCCTAGAAGCAGCATCTTCAATAGAGATCTTAAGCCCATGAA 420
TTATATAGGACCTGACTCAGTTTCACAGATTAATTCACCCCACATTGATATGGAAAGCAA 480
AATTTTATTTGATCAAATGCATCTTTGGTGAATTTCGAGCCATCTGATGATGGGAAAATT 540
AAATGTAGAAGTCTATGCCTCAAAGACCTACTAAGTTATAAAACAATAATTGTGGTAGGC 600
CAGCAATTGCTTTAACCTTTATTAAGCATTGTCTTTTATTTATTCATAGGCTCTTGCAGG 660
ATGGATTTTCAAGGGTCAGTTCCGACCTATATCTATGACATCGATTAtGGTATGTCAGCA 720
MetAspPheGlnGlySerValProThrTyrIleTyrAspIleAspTyrGlyMetSerAla
CCCTGCCAAAAAATCAATGtGAAACAAATTGCAGCTcAGCTCCtgCCCCAcTATACTCC 780
ProCysGlnLysIleAsnValLysGlnIleAlaAlaGlnLeuLeuProProLeuTyrSer
ctGGTATTCATCTttGGTTTtGcGGGAAACATGATGGTcTTCCTCATCTTGATAAGCTGC 840
LeuValPheIlePheGlyPheAlaGlyAsnMetMetValPheLeuIleLeuIleSerCys
AAAAAGCTGAAGAGCGTGACTGATATCTATCTGCTCAACTTGGCCATCTCtGACCTGcTC 900
LysLysLeuLysSerValThrAspIleTyrLeuLeuAsnLeuAlaIleSerAspLeuLeu
TTCCTGCTCACACTACCATTCTGGGCTCACTATGCTGCAAATGAGTGGATCTTTGGGAAT 960
PheLeuLeuThrLeuProPheTrpAlaHisTyrAlaAlaAsnGluTrpIlePheGlyAsn
ATAATGTGTAAAGTATTCACAGGTGTCTATCATATTGGTTATTTTGGTGGAATCTTCTTC 1020
IleMetCysLysValPheThrGlyValTyrHisIleGlyTyrPheGlyGlyIlePhePhe
ATTATCCTCCTGACAATTGATAGGTACTTGGCTATTGTCCATGCTGTGTtGCTTTAAAA 1080
IleIleLeuLeuThrIleAspArgTyrLeuAlaIleValHisAlaValPheAlaLeuLys
GTCACAACGGTCAACTTTGGGGTGATAACAAgTGTAGTCACTTGGGTGGTGGCTGTGTTT 1140
ValThrThrValAsnPheGlyValIleThrSerValValThrTrpValValAlaValPhe
GCCTCTCTCCCAgAAATAATCTtTACCAgATCTCAgAAAgAAGGTTtTCATTATACATGC 1200
AlaSerLeuProGluIleIlePheThrArgSerGlnLysGluGlyPheHisTyrThrCys
```

Fig. 1

```
AGTCCTCATTTTCCACACACTCAGTATCATTTCTGGAAGAGTTTCCAAACATTAAAGATG  1260
SerProHisPheProHisThrGlnTyrHisPheTrpLysSerPheGlnThrLeuLysMet

GTCATCTTGAGCCTGATCCTGCCTCTACTTGTCATGATCATCTGCTACTCAGGAATTCTC  1320
ValIleLeuSerLeuIleLeuProLeuLeuValMetIleIleCysTyrSerGlyIleLeu

CACACCCTGTTTCGCTGTAGGAATGAGAAGAAGAGGCACAGGGCTGTGAGGCTCATCTTT  1380
HisThrLeuPheArgCysArgAsnGluLysLysArgHisArgAlaValArgLeuIlePhe

GCCATCATGATTGTCTACTTTCTCTTCTGGACTCCCTACAACATTGTCCTCCTCCTGACC  1440
AlaIleMetIleValTyrPheLeuPheTrpThrProTyrAsnIleValLeuLeuLeuThr

ACCTTCCAGGAATTCTTTGGACTGAATAACTGCAGTAGTTCTAATAGACTAGACCAGGCC  1500
ThrPheGlnGluPhePheGlyLeuAsnAsnCysSerSerSerAsnArgLeuAspGlnAla

ATGCAGGCAACAGAGACTCTTGGAATGACACACTGCTGCCTAAACCCTGTCATCTATGCC  1560
MetGlnAlaThrGluThrLeuGlyMetThrHisCysCysLeuAsnProValIleTyrAla

TTTGTTGGAGAgAAGTTCCGGAGTTATCTCTCAGTGTTCTTCCGAAAACACATTGTCAAA  1620
PheValGlyGluLysPheArgSerTyrLeuSerValPhePheArgLysHisIleValLys

CGCTTTTGCAAACGGTGTTCAATTTTCCAGCAAGACAATCCTGATCGTGTAAGCTCAGTC  1680
ArgPheCysLysArgCysSerIlePheGlnGlnAspAsnProAspArgValSerSerVal

TATACCCGATCCACAGGAGAACATGAAGTTTCTACTGGTTTATGACCTGGTTGACTTTTG  1740
TyrThrArgSerThrGlyGluHisGluValSerThrGlyLeu

TGTATCACGTAGTTTTTCTATGCAGCTTGGGAGTAGGAATGGTTCTTTTAAAAAAGAAAT  1800

TAGTATCATAGAGGGCCCAAGATACATGCATCTTTTTGATATTTATTTTTAGATAGATTG  1860

GATCTTTTAAAACTGAATGGGGAGGTTGGGGTGGGGGAGCAgGGAgAACGAgTCTTTTAT  1920

CAGGGCCGGGAAATATGCACAAAGAgACTTGAGTCAGGTGCCATGACCCATATGCAAAGG  1980

GACGGACACAGGGCCgATGCTGTTGCCTAgAAATGACGTGTCTCCCCGCTGGGTTCCTGA  2040

AAGGCGGCTGTAAATATGCCTGATTGCCATAAAGTCGCTTCTTGCTGTCTATGGATGTGC  2100

CTGACTGCCAACAGGGAAGAACCACTTCTGCATATAAAATGTAGAGTCAGCAGAACTTGG  2160

GGTAAATTGAAGTTAGAGGTGCATAAGAACCCCTAGGCTTAGTTAGGTTGAAATACCCAT  2220

TGAGGAAACAGCAAATACAAAGGAAGAATAAAGAGTTTAGCCGGGAAGGTAGTCTCATTT  2280

TACAGCCGGAATATAATGTTATCTCAGGCTAGCATTTTGTTCCTGCCTTCAGACCTAAAT  2340

CCTACCACACCGGGACTGTGAAACACCTGGATTATGAATCATGAgCCTGAgGTCTAgGAA  2400

TAATAACGTTTGTgATTTTAgATgAGGGCTGTTTACATAgTTTGA  2445
```

Fig. 1 cont'd

Nucleotide sequence of human clone HDGNR10, a RANTES receptor also identified as human CC-CKR5

```
   1  ATGGATTATC AAGTGTCAAG TCCAATCTAT GACATCAATT ATTATACATC
  51  GGAGCCCTGC CAAAAAATCA ATGTGAAGCA AATCGCAGcC CGCCTCCTGC
 101  CTCCGCTCTA CTCACTGGTG TTCATCTTTG GTTTtGTGGG CAACATGCTG
 151  GTCATCCTCA TCCTGATAAA CTGcAAAAGG CTGAAGAGCA TGACTGACAT
 201  CTaCCTGCTC AACCTGGCCA TCTCTGACCT GTTTTTCCTT CTTACTGTCC
 251  CCTTCTGGGC TCACTATGCT GCCGCCCAGT GGGACTTTGG AAATACAATG
 301  TGTCAACTCT TGACAGGGCT CTATTTTATA GGCTTCTTCT CTGGAATCTT
 351  CTTCATCATC CTCCTGACAA TCGATAGGTA CCTGGCTGTC GTCCATGCTG
 401  TGTTTGCTTT AAAAGCCAGG ACGGTCACCT TTGGGGTGGT GACAAGTGTG
 451  ATCACTTGGG TGGTGgCTGT GTTTGCGTCT CTCCCAGGAA TCATCTTTAC
 501  CAGATCTCAA AAAGAAGGTC TTCATTACAC CTGCAGCTCT CATTTTCCAT
 551  ACAGTCAGTA TCAATTCTGG AAGAATTTCC AGACATTAAA GATAGTCATC
 601  TTGGGGCTGG TCCTgCCgCT GCTTGTCATG GTCATCTGCT ACTCGGGAAT
 651  CCTAAAAACT CTGCTTCGGT GTCGAAATGA GAAGAAGAGG CACAGGGCTG
 701  TGAGGCTTAT CTTCACCATC ATGATTGTTT ATTTTCTCTT CTGGGCTCCC
 751  TACAACAtTG TCCTTCTCCT GAACACCTTC CAGGAATTCT TTGGCCTGAA
 801  TAATTGCAGT AGCTCTAACA GGTTGGACCA AGCTATGCAG GTGACAGAGA
 851  CTCTTGGGAT GACGCACTGC TGCATCAACC CCATCATCTA TGCCTTTGTC
 901  GGGGAGAAGT TCAGAAACTA CCTCTTAGTC TTCTTCCAAA AGCACATTGC
 951  CAAACGCTTC TgCAAATGCT GTTCTATTTT CCAGCAAGAG GCTCCCGAGC
1001  GAGCAAGCTC AGTTTACACC CGATCCACTG ggGAGCAGGA AATATCTGTG
1051  GGCtTGTGA
```

Fig. 2

MOUSE CC-CKR5 RECEPTOR POLYPEPTIDE

FIELD OF THE INVENTION

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of a mouse chemokine receptor, hereinafter referred to as "mouse CC-CKR5".

BACKGROUND OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptides of the present invention are chemokine receptors. The invention also relates to inhibiting or activating the action of such polypeptides.

Chemokines are small signaling proteins that can be divided into two subfamilies, CC-chemokines or CXC-chemokines, depending upon the relative position of the first two conserved cysteines. A number of chemokines, including interleukin-8, RANTES, MCP-1, MCP-2, MCP-3, GROα, GROβ, GROγ, MIP-1α, and MIP-1β have been described. See, e.g. Baggiolini et al., ADVANCES IN IMMUNOLOGY (Dixon, F.J., Ed.)Vol. 55, pages 97–179, Academic Press, New York 1994. Chemokines attract and stimulate specific subsets of leukocytes and thus are very important regulators in the physiology of acute and chronic inflammatory processes. Oppenheim et al., *Annu. Rev. Immunol.*, 1991, 9:617–648. For example, RANTES is a chemoattractant for monocytes, memory T-cells and eosinophils and induces the release of histamine by basophils. MCP-1, which is released by smooth muscle cells in arteriosclerotic lesions, is believed to be a factor responsible for macrophage attraction leading to the progressive aggravation of these lesions.

Recent studies have demonstrated that the actions of both CC- and CXC-chemokines are mediated by subfamilies of G-protein coupled receptors. Several functional receptors for CC and CXC chemokines have been identified in humans. For example, two receptors for interleukin-8 have now been identified. Holmes et al., *Science*, 1991, 253:1278–1283 and Murphy, P.M. and Tiffany, H.L. *Science*, 1991, 253:1280–1283. The first, IL-8RA, binds interleukin-8 specifically, while the second, IL,-8RB, binds IL-8 and other CXC-chemokines such as GRO. Several CC-chemokine receptors have also been identified. A receptor designated CC-chemokine receptor 1 or CC-CKR1 which binds both RANTES and MIP-1α was identified by Neote et al., *Cell*, 1993, 72:415–425. A second CC chemokine receptor CC-CKR2 which binds to MCP-1 and MCP-3 has also been identified. Charo et al., *Proc. Nat'l Acad. Sci. USA*, 1994, 91:2752–2756; Yamagami et al., *Biochem. Biophys. Res. Commun.*, 1994, 202:1156–1162 ; Franci et al.,*J. Immunol.*, 1995, 154:6511–6517. CC chemokine receptors, CC-CKR3 and CC-CKR4, have also been identified. See, Combadiere et al., *J. Biol. Chem.* 1995, 270:16491–16494; Correction *J. Biol. Chem.*, 1995, 270:30235 and Power et al., *J. Biol. Chem.*, 1995, 270:19495–19500, respectively.

Molecular cloning and functional expression of a human receptor, ChemR13, was recently reported. Samson et al. *Biochemistry*, 1996, 35:3362–3367. The gene encoding ChemR13 is physically linked with the CC-CKR2 receptor gene in the human genome. The ChemR13 receptor, stably transfected in CHO-K1 cells was found to be stimulated by MIP-1α, MIP-1β, and RANTES, while MCP-1, MCP-2, MCP-3, IL-8 and GROαx had no effect. This new human CC-chemokine receptor has been designated CC-CKR5.

A chemokine like orphan 7TM receptor, referred to as fusin, was also recently identified which is capable of acting as co-factor for the entry of the HIV-1 virus into T cells. Feng et al., *Science*, 1996, 272:872. Human CC-CKR5 receptor has also been reported as a principle cofactor in the entry of macrophage-tropic HIV-1 viruses into cells. These viruses are believed to be the primary pathogenic strain in vivo. Deng et al., *Nature*, 1996, 381:661; Dragic et al., *Nature*, 1996, 381:667.

A mouse ortholog of the human CC-CKR5 receptor has now been identified. Accordingly, it is now possible to knock out the mouse CC-CKR5 receptor gene from a mouse strain, replacing the mouse gene with human CC-CKR5 receptor gene to create a mouse model for human immunodeficiency virus. This mouse model is also useful in studying the role of this chemokine receptor in T-cell mediated inflammation.

SUMMARY OF THE INVENTION

Toward these ends, and others, it is all object of the present invention to provide polypeptides, inter alia, that have been identified as novel mouse CC-CKR5 by homology between the amino acid sequence set out in FIG. 1 and the known amino acid sequence of human CC-CKR5.

It is a further object of the invention to provide polynucleotides that encode mouse CC-CKR5, particularly polynucleotides that encode the polypeptide herein designated mouse CC-CKR5.

In a particularly preferred embodiment of this aspect of the invention, the polynucleotide comprises the region encoding mouse CC-CKR5 in the sequence set out in FIG. 1.

In accordance with this aspect of the present invention, there is provided an isolated nucleic acid molecule encoding a mature polypeptide expressible from the mouse gene contained in ATCC Deposit No. 98170.

In accordance with this aspect of the invention, there are provided isolated nucleic acid molecules encoding mouse CC-CKR5, including mRNAs, genomic DNAs and fragments and, in further embodiments of this aspect of the invention, biologically, diagnostically, clinically or therapeutically useful variants, analogs or derivatives thereof, including fragments of the variants, analogs and derivatives.

In accordance with another aspect of the present invention, there are provided methods of generating a mouse model for screening for compounds which bind to and activate or inhibit activation of the human CC-CKR5 receptor.

In accordance with another object the invention, there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing human CC-CKR5 expression by determining CC-CKR5 polypeptides or CC-CKR5-encoding mRNA; to treat T-cell mediated inflammation and more specifically HIV-infection, in vivo by exposing mice expressing human CC-CKR5 to a CC-CKR5 polypeptide or polynucleotide to augment CC-CKR5 function or remediate CC-CKR5 dysfunction.

In accordance with still another embodiment of the present invention, there is provided a process of using such activating compounds to stimulate the CC-CKR5 receptor for the treatment of conditions related to the under-expression of this receptor.

In accordance with another aspect of the present invention, there is provided a process of using such inhibiting compounds for treating conditions associated with over-expression of the CC-CKR5 receptor.

In accordance with yet another aspect of the present invention, there is provided non-naturally occuring recombinant CC-CKR5 polypeptides which are fragments, consensus fragments and/or sequences having conservaitive amino acid substitutions of at least one domain of the mouse CC-CKR5 of the present invention, such that the receptor may bind human CC-CKR5 ligands, or which may also modulate, quantitatively or qualitatively, human CC-CKR5 ligand binding.

In accordance with still another aspect of the present invention, there are provided synthetic or recombinant mouse CC-CKR5 polypeptides, conservative substitution and derivatives thereof, antibodies thereto, anti-idiotype antibodies, compositions and methods that can be useful as potential modulators of human CC-CKR5 function, by binding to ligands or modulating ligand binding, due to their expected biological properties, which may be used in diagnostic, therapeutic and/or research applications.

It is still another object of the present invention to provide recombinant polypeptides which are designed to inhibit or mimic various mouse CC-CKR5 or fragments thereof, as receptor types and subtypes.

In accordance with certain preferred embodiments of this and other aspects of the invention, there are provided probes that hybridize to CC-CKR5 sequences.

In certain additional preferred embodiments of this aspect of the invention, there are provided antibodies against mouse CC-CKR5 polypeptides. In certain particularly preferred embodiments in this regard, the antibodies are highly selective for mouse and human CC-CKR5.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 shows the nucleotide sequence (SEQ ID NO:1) and deduced amino acid sequence (SEQ ID NO:2) of mouse CC-CKR5.

FIG. 2 shows the nucleotide sequence (SEQ ID NO:3) of human clone HDGNR10, a RANTES receptor also identified as human CC-CKR5.

GLOSSARY

The following illustrative explanations are provided to facilitate understanding of certain terms used frequently herein, particularly in the examples. The explanations are provided as a convenience and are not meant to limit the invention.

"Digestion" of DNA refers to catalytic cleavage of a DNA with an enzyme such as, but not limited to, a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 microgram of plasmid or DNA fragment is digested with about 2 units of enzyme in about 20 microliters of reaction buffer. For the purpose of isolating DNA fragments for plasmid construction, typically 5 to 50 micrograms of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

"Genetic element" generally means a polynucleotide comprising a region that encodes a polypeptide or a region that regulates replication, transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukatyotic cells. Genetic elements also may be comprised within a host cell genome, not in their natural state but, rather, following manipulation such as isolation, cloning and introduction into a host cell in the form of purified DNA or in a vector, among others.

"Isolated" means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media, formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term is it is employed herein.

"Ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y., 1989, hereinafter referred to as Sambrook et al.

"Oligonucleotide(s)" refers to relatively short polynucleotides. Often the term refers to single-stranded deoxyribonucleotides, but it cain refer as well to single-or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, will readily form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

"Plasmids" are genetic elements that are stably inherited without being a part of the chromosome of their host cell. They may be comprised of DNA or RNA and may be linear or circular. Plasmids code for molecules that ensure their replication and stable inheritance during cell replication and may encode products of considerable medical, agricultural and environmental importance. For example, they code for toxins that greatly increase the virulence of pathogenic bacteria. They can also encode genes that confer resistance to antibiotics. Plasmids are widely used in molecular biology as vectors used to clone and express recombinant genes. Plasmids generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

"Polynucleotide(s)" generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single-and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotidle includes DNAs or RNAs as described above that contain one or more modified bases. Thus, DNAs or RNAs with backbones modified for stability or for other reasons are polynucleotides as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide, as it is employed herein, embraces such chemically, enzymatically or metabolically modified forms of polynucleotides, as well as the chemical forms of DNA and RNA characteristic of viruses and cells, including inter alia simple and complex cells.

"Polypeptides", as used herein, includes all polypeptides as described below. The basic structure of polypeptides is well known and has been described in innumerable textbooks and other publications in the art. In this context, the term is used herein to refer to any peptide or protein comprising two or more aimino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, or by chemical modification techniques which are well known to the art. Even the common modifications that occur naturally in polypeptides are too numerous to list exhaustively here, but they are well described in basic texts and in more detailed monographs, as well as in a voluminous research literature, and thus are well known to those of skill in the art.

Examples of known modifications which may be present in polypeptides of the present invention include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gramma-carboxylation, glycosylation, GPI anchor formation, hydroxylation, iodination, melhylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications such as glycosylation, lipid attachment, sulfation, gamma-carboxylation of glutamic acid residues, hydroxylation and ADP-ribosylation are described in basic texts such as PROTEINS—STRUCTURE AND MOLECULAR PROPERTIES, 2nd Ed., T. E. Creighton, W. H. Freeman and Company, New York, 1993. Detailed reviews are also available on this subject. See e.g. Wold, F., Posttranslational Protein Modifitications: Perspectives and Prospects, pages 1–12 in POSTTRANSLATIONAL COVALENT MODIFICATION OF PROTEINS, B. C. Johnson, Ed., Academic Press, New York, 1983; Seifter et al., *Meth. Enzymol.*, 1990, 182:626–646 and Rattan et al., *Ann. N.Y. Acad. Sci.*, 1992, 663: 48–62.

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell's posttranslational modification capacity and the modification signals present in the polypeptide amino acid sequence. For instance, as is well known, glycosylation often does not occur in bacterial hosts such as *E. Coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having the native patterns of glycosylation, inter alia. Similar considerations apply to other modifications.

It will be appreciated that the same type of modification may be present in the same or varying degrees at several sites in a given polypeptide. Also, a given polypeptide may contain many types of modifications.

In general, as used herein, the term polypeptide encompasses all such modifications, particularly those that are present in polypepltides synthesized by expressing a polynucleotide in a host cell.

"Variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail.

Variants include polynucleotides that differ in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type, a variant will encode a polypeptide with the same amino acid sequence as the reference. As also noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

Variants also include polypeptides that differ in amino acid sequence from another, reference polypeptide. Generally, differences ale limited so that the sequences of the reference and the variant are closely similar overall and, in many regions, identical.

A variant and reference polypeptide may differ in amino acid sequence by one or more substitutions, additions and deletions, which may be present in any combination.

"Fusion protein" as the term is used herein, is a protein encoded by two, often unrelated fused genes or fragments thereof.

"Binding molecules" (or otherwise called "interaction molecules" or "receptor component factors") refer to molecules other than ligands that specifically bind to or interact with receptor polypeptides of the present invention. Such binding molecules are a part of the present invention. Binding molecules may also be non-naturally occurring, such as antibodies and antibody-derived reagents that bind specifically to polypeptides of the invention.

As known in the art, "similarity" between two polypeptides is determined by comparing the amino acid sequence and its conserved amino acid substitutes of one polypeptide to the sequence of a second polypeptide. Moreover, also known in the art is "identity" which means the degree of sequence relatedness between two polypeptide or two polynucleotide sequences as determined by the identity of the match between two strings of such sequences. Both identity and similarity can be readily calculated (COMPUTATIONAL MOLECULAR BIOLOGY, Lesk, A.M., ed., Oxford University Press, New York, 1988; BIO- COMPUTING: INFORMATICS AND GENOME PROJECTS, Smith, D.W., ed., Academic Press, New York, 1993; COMPUTER ANALYSIS OF SEQUENCE DATA, PART I, Griffin, A.M., and Griffin, H.G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity and similarity between two polynucleotide or polypeptide sequences, the terms "identity" and "similarity" are well known to skilled artisans (Carillo, H., and Lipton, D., *SIAM J. Applied Math.*, 1988, 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J. Applied Math.*, 1988, 48:1073. Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, J., et al., *Nucleic Acids Research,* 1984, 12(1):387), BLASTP, BLASTN, FASTA (Atschul, S.F. et al., *J. Molec. Biol.,* 1990, 215:403).

DETAILED DESCRIPTION OF THE INVENTION

The present invention relates to novel mouse CC-CKR5 polypeptides and polynucleotides, among other things, as described in greater detail below. In particular, the invention relates to polypeptides and polynucleotides of a novel mouse CC-CKR5, which is related by amino acid sequence homology to human CC-CKR5. The invention relates especially to mouse CC-CKR5 having the nucleotide and amino acid sequences set out in FIG. 1, and to the mouse CC-CKR5 nucleotide sequence of the gene in ATCC Deposit No. 98170 which is herein referred to as "the deposited clone" or as the "gene in the deposited clone" and the amino acid sequence encoded thereby. It will be appreciated that the nucleotide and amino acid sequences set out in FIG. 1 are obtained by sequencing the gene of the deposited clone. Hence, the sequence of the deposited clone is controlling as to any discrepancies between the two and any reference to the sequences of FIG. 1 includes a reference to the sequence of the mouse gene in the deposited clone.

Polynucleotides

In accordance with one aspect of the present invention, there are provided isolated polynucleotides which encode the mouse CC-CKR5 polypeptide having the deduced amino acid sequence of FIG. 1.

Using the information provided herein, such as the polynucleotide sequence set out in FIG. 1 and in SEQ ID NO:1, a polynucleotide of the present invention encoding mouse CC-CKR5 may be obtained using standard cloning and screening procedures, such as those for cloning genes from a mouse genomic lambda library using human cDNA sequences as hybridization probes. Illustrative of the invention, the polynucleotide set out in FIG. 1 was discovered in a mouse strain 129 SVJ genomic lambda library (Cat #946309; Stratagene, La Jolla, Calif.) using the coding region of clone HDGNR10(see FIG. 2, SEQ ID NO:3) as a hybridization probe. Using this method, one genomic clone observed to hybridize to this probe was isolated, purified and characterized by DNA sequencing.

Mouse CC-CKR5 of the invention is structurally related to other proteins of the G coupled protein receptor family, as shown by the results of sequencing the gene encoding mouse CC-CKR5 in the deposited clone. The mouse CC-CKR5 contains seven hydrophobic regions of approximately 20–30 amino acids each, which are typically found among the G-protein linked superfamily of receptors. More significantly, this protein shares 90.6% similarity and 81.8% identity over its entirety with the human CC-CKR5. The overall nucleotide sequence identity is 83.9%. This degree of sequence conservation is consistent with the conclusion that the encoded receptor represents the mouse complement of the human CC-CKR5 receptor. This clone shares lesser homology with other known human CC-CKR receptor proteins such as CC-CKR2 (74% identity), human CC-CKR1 (55% identity), mouse CC-CKR1 (53% identity), mouse CC-CKR4 (50% identity) and human CC-CKR4 (48% identity). The gene sequence obtained is set out in FIG. 1 and also SEQ ID NO: 1. The open reading frame of this clone was identified by reverse translation of the DNA sequence and found to encode a protein of 354 amino acids, also set out in FIG. 1 and SEQ ID NO:2.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may he the non-coding strand, also referred to as the anti-sense strand.

The coding sequence which encodes the polypeptide may be identical to the coding sequence of the polynucleotide shown in FIG. 1, SEQ ID NO: 1. It may also be a polynucleotide with a different sequence, which, as a result of the redundancy (degeneracy) of the genetic code, also encodes the polypeptide of FIG. 1, SEQ ID NO: 2.

Polynucleotides of the present invention which encode the polypeptide of FIG. 1 may include, but are not limited to, the coding sequence for the mature polypeptide, by itself; the coding sequence for the mature polypeptide and additional coding sequences; and the coding sequence of the mature polypeptide, with or without the aforementioned additional coding sequences, together with additional, non-coding sequences. Examples of additional coding sequences include, but are not limited to, sequences encoding a leader or secretory sequence, such as a pre-, or pro- or preproprotein sequence. Examples of additional noncoding sequences include, but are not limited to, introins and non-coding 5' and 3' sequences, such as the transcribed, non-translated sequences that play a role in transcription and mRNA processing, including splicing and polyadenylation signals, for example, for ribosome binding and stability of mRNA. Coding sequences which provide additional functionalities may also be incorporated into the polypeptide. Thus, for instance, the polypeptide may be fused to a marker sequence, such as a peptide, which facilitates identification of the expressed receptor on the cell surface. In certain preferred embodiments of this aspect of the invention, the marker sequence is a peptide such as the HA tag. The HA tag corresponds to an epitope derived of influenza hemagglutinin protein, which has been described by Wilson et al., *Cell,* 1984, 37:767. Many other such tags are commercially available.

In accordance with the foregoing, the term "polynucleotide encoding a polypeptide" as used herein encompasses polynucleotides which include, by virtue of the redundancy of the genetic code, any sequence encoding a polyleptide of the present invention, particularly the mouse CC-CKR5 having the amino acid sequence set out in FIG. 1. The term also encompasses polynucleotides that include a single continuous region or discontinuous regions encoding the polypeptide (for example, interrupted by introns) together with additional regions, that also may contain codinig and/or non-coding sequences.

The present invention further relates to variants of the herein above described polynucleotides which encode for fragments, analogs and derivatives of the polypeptide having the deduced amino acid sequence of FIG. 1. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of mouse CC-CKR5 set out in FIG. 1; variants, analogs, derivatives and fragments thereof, and fragments of the variants, analogs and derivatives.

Further particularly preferred in this regard are polynucleotides encoding mouse CC-CKR5 variants, analogs, derivatives and fragments, and variants, analogs and derivatives of the fragments, which have the amino acid sequence of the mouse CC-CKR5 polypeptide of FIG. 1 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the mouse CC-CKR5. Also especially preferred in this regard are conservative substitutions. Most highly preferred are polynucleotides encoding polypeptides having the amino acid sequence of FIG. 1, without substitutions.

Further preferred embodiments of the invention are polynucleotides that are at least 85% identical to a polynucleotide encoding the mouse CC-CKR5 polypeptide having the amino acid sequence set out in FIG. 1, and polynucleotides which are complementary to such polynucleotides. In this regard, polynucleotides at least 90% identical to the same are particularly preferred, and those with at least 95% are more particularly preferred. Furthermore, those with at least 97% are highly preferred and those with at least 98–99% are more highly preferred, with at least 99% being the most preferred.

Particularly preferred embodiments in this respect, moreover, are polynucleotides which encode polypeptides which retain substantially the same biological function or activity as the mature polypeptide encoded by the gene of FIG. 1.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as hybridization probes for cDNA and genomic DNA, to isolate full-length cDNAs and genomic clones encoding mouse CC-CKR5 and to isolate cDNA and genomic clones of other genes that have a high sequence similarity to mouse CC-CKR5 gene. Such probes generally will comprise at least 15 nucleotides. Preferably, such probes will have it least 30 nucleotides and may have at least 50 nucleotides. Particularly preferred probes will range between 30 and 50 nucleotides.

For example, the coding region of the mouse CC-CKR5 gene may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine the members of the library to which the probe hybridizes to.

The polynucleotides and polypeptides of the present invention may be employed as research reagents and materials for discovery of treatments and diagnostics to human disease, as further discussed herein relating to polynucleotide assays.

Deposited Materials

A deposit containing a mouse CC-CKRF gene has been made with the American Type Culture Collection, 10801 University Boulevard, Manassas, Va. 20110-2209, USA, on Sep. 18, 1996, and assigned ATCC Deposit No. 98170. The mouse gene deposit is referred to herein as "the deposited clone" or as "the gene in the deposited clone".

The deposited material is an *E. coli* mHDGNR10:pBluescript/DH5α (Stratagene, La Jolla, Calif.) that contains the full length mouse CC-CKR5 gene, referred to as "mHDGNR10/pBluescript" upon deposit.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials. No such license is hereby granted.

Polypeptides

The present invention further relates to a mouse CC-CKR5 polypeptide which has the deduced amino acid sequence of FIG. 1, SEQ ID NO: 2.

The invention also relates to fragments, analogs and derivatives of these polypeptides. The terms "fragment," "derivative" and "analog" when referring to the polypeptide of FIG. 1, mean a polypeptide which retains essentially the same biological function or activity as such polypeptide, i.e. functions as a mouse CC-CKR5, or retains the ability to bind the ligand or the binding molecules even though the polypeptide does not function as a mouse CC-CKR5, for example, a soluble form of the receptor. Thus, an analog includes, for example, a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments, it is a recombinant polypeptide.

The fragment, derivative or analog of the polypeptide of FIG. 1 may be (i) one in which one or more of the amino acid residues are substituted with a conserved or non-conserved amino acid residue (preferably a conserved amino acid residue) and such substituted amino acid residue may or may not be one encoded by the genetic code; (ii) one in which one or more of the amino acid residues includes a substituent group; or (iii) one in which the additional amino acids are fused to the mature polypeptide, such as a sequence which is employed to detect cell surface expression of the polypeptide. Such fragments, derivatives and analogs are deemed to be within the scope of those skilled in the art from the teachings herein.

Among the particularly preferred embodiments of the invention in this regard are polypeptides having the amino acid sequence of mouse CC-CKR5 set out in FIG. 1, variants, analogs, derivatives and fragments thereof, and variants, analogs and derivatives of the fragments. Further particularly preferred embodiments of the invention in this regard are polypeptides having the amino acid sequence of mouse CC-CKR5, variants, analogs, derivatives and fragments thereof, and variants, analogs and derivatives of the fragments which retain the activity/function of mouse CC-CKR5.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further particularly preferred in this regard are variants, analogs, derivatives and fragments, and variants, analogs and derivatives of the fragments, having the amino acid sequence of the mouse CC-CKR5 polypeptide of FIG. 1, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the mouse CC-CKR5. Also especially preferred in this regard are conservative substitutions. Most highly preferred are polypeptides having the amino acid sequence of FIG. 1 without substitutions.

The polypeptides and polynucleotides of the present invention are preferably expressed on the cell surface of mammalian cells and functionally coupled to G-proteins.

The polypeptides of the present invention include the polypeptide of SEQ ID NO: 2 (in particular the mature polypeptide) as well as polypeptides which have at least 85% identity to the polypeptide of SEQ ID NO: 2 and more preferably at least 90% similarity (more preferably at least 90% identity) to the polypeptide of SEQ ID NO: 2 and still more preferably at least 95% similarity (still more preferably at least 95% identity) to the polypeptide of SEQ ID NO:2.

Vectors, Host Cells, Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation may also be used to introduce polynucleotides into a host. If the vector is a virus, it may he packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. which is illustrative of the many laboratory manuals that detail these techniques.

In accordance with this aspect of the invention the vector may be, for example, a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors may also be and preferably are introduced into cells as packaged or encapsidated virus by well known techniques for infection and transduction. Viral vectors may be replication competent or replication defective. In the latter case, viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors are either supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific expression. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression, generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from viruses such as baculoviruses, papova viruses, SV40, vaccinia viruses, adenoviruses, fowl pox viruses, pseudorabies viruses, alphaviruses and retroviruses, and vectors derived from combinations thereof. Generally, any vector suitable to maintain, propagate or express polynucleotides to produce a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skilled in the art, are set forth in great detail in Sambrook et al.

The DNA sequence in the expression vector is operatively linked to appropriate expression control sequence(s), including, for instance, a promoter to direct mRNA transcription. Representatives of such promoters include the SV40 early and late promoters and promoters of retroviral LTRs, to name just a few of the well-known promoters. It will be understood that numerous other promoters useful in this aspect of the invention are well known and may be routinely employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, i.e. as enhancers.

Vectors for propagation and expression generally will include selectable markers. Selectable marker genes provide a phenotypic trait for selection of transformed host cells. Preferred markers include, but are not limited to, dihydrofolate reductase or neomycin resistance for eukaryotic cell culture. Such markers may also be suitable for amplification. Alternatively, the vectors may contain additional markers for this purpose.

The vector containing the appropriate DNA sequence as described elsewhere herein, as well as an appropriate promoter, and other appropriate control sequences, may be introduced into an appropriate host using a variety of well known techniques suitable for expression therein of a desired polypeptide. Representative examples of appropriate hosts include, but are not limited to, insect cells Such as Drosophila S2 and Spodoptera Sf9 cells; and animal cells such as CHO, COS and Bowes melanoma cells. Hosts of a great variety of expression constructs are well known, and those of skill will be enabled by the present disclosure to routinely select a host for expressing a polypeptide in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of a restriction site or sites for introducing a candidate promoter fragment; i.e., a fragment that may contain a promoter. As is well known, introduction into the vector of a promoter-containing fragment at the restriction site upstream of the CAT gene engenders production of CAT activity, which can be detected by standard CAT assays. Vectors suitable to this end are well known and readily available. Two examples of such vectors include pKK232-8 and pCM7. Thus, promoters for expression of polynucleotides of the present invention include not only well known and readily available promoters, but also promoters that may be readily obtained by the foregoing technique, using a reporter gene.

Among known eukaryotic promoters suitable in this regard are the CMV immediate early promoter, the HSV thymidine kinase promoter, the early and late SV40 promoters, the promoters of retroviral LTRs, such as those of the Rous Sarcoma Virus("RSV"), and metallothionein promoters, such as the mouse metallothionein-I promoter.

Selection of appropriate vectors and promoters for expression in a host cell is a well known procedure and the requisite techniques for construction of expression vectors, introduction of the vector into the host and expression in the host are routine skills in the art.

The present invention also relates to host cells containing the above-described constructs. The host cell can be a higher eukaryotic cell, such as a mammalian cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals.

Constructs in host cells can be used in a conventional manner to produce the gene product encoded by the recombinant sequence.

Mature proteins can be expressed in mammalian cells under the control of appropriate promoters. Appropriate cloning and expression vectors for use with prokaryotic and eukaryotic hosts are described by Sambrook et al.

Transcription of DNA encoding the polypeptides of the present invention by higher eukaryotes may be increased by inserting an enhancer sequence into the vector. Enhancers are cis-acting elements of DNA, usually from about 10 to 300 bp, that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

A polynucleotide of the invention encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and a polyadenylation signal and transcription termination signal appropriately disposed at the 3' end of the transcribed region.

The polypeptide may be expressed in a modified form, such as a fusion protein, and may include not only secretion signals but also additional heterologous functional regions. A region may also be added to the polypeptide to facilitate cell surface expression. The addition of peptide moieties to polypeptides to engender detection is familiar using routine techniques to those skilled in the art.

Various mammalian cell culture systems can be employed for expression, as well. Examples of mammalian expression systems include the C127, 3T3, CHO, HeLa, human kidney 293 and BHK cell lines. and the COS-7 line of monkey kidney fibroblasts, described by Gluzman et al., Cell, 1981, 23:175. Other cell lines capable of expressing a compatible vector include for example, Mammalian expression vectors will comprise an origin of replication, a suitable promoter and enhancer, and any necessary ribosome binding sites, polyadenylation sites, splice donor and acceptor sites, transcriptional termination sequences, and 5' flanking non-transcribed sequences that are necessary for expression. In certain preferred embodiments, DNA sequences derived from the SV40 splice sites and the SV40 polyadenylation sites are used for required non-transcribed genetic elements.

Mouse CC-CKR5 polynucleotides and polypeptides may be used in accordance with the present invention for a variety of applications, particularly those that make use of the chemical and biological properties of mouse CC-CKR5. Additional applications relate to diagnosis and to treatment of disorders of cells, tissues and organisms. These aspects of the invention are illustrated further by the following discussion.

Antibodies

The polypeptides, their fragments or other derivatives, or analogs thereof, or cells expressing them can also be used as immunogens to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., Nature, 1975, 256:495–497), the trioma technique, the human B-cell hybridoma technique (Kozbor et al., Immunology Today, 1983, 4:72) and the EBV-hybridoma technique (Cole et al., MONOCLONAL ANTIBODIES AND CANCER THERAPY, pages 77–96, Alan R. Liss, Inc., 1985).

Techniques described for the production of single chain antibodies (U.S. Pat. No. 4,946,778) can also be adapted to produce single chain antibodies to immunogenic polypeptide products of this invention. Also, transgenic mice, or other organisms including other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Antibodies against mouse CC-CKR5 may also be employed to inhibit T-cell mediated inflammation and HIV-1 infection, among others.

Mouse CC-CKR5 Binding Molecules and Assays

Mouse CC-CKR5 can also be used to isolate proteins which interact with it; this interaction can be a target for interference. Inhibitors of protein-protein interactions between mouse CC-CKR5 and other factors could lead to the development of pharmaceutical agents which modulate human CC-CKR5 receptor activity.

Thus, this invention also provides a method for identification of binding molecules to mouse CC-CKR5. Genes encoding proteins for binding molecules to mouse CC-CKR5 can be identified by numerous methods known to those of skill in the art, for example, radioligand binding assays, calcium mobilization assays, ligand panning and FACS sorting. Such methods are described in many laboratory annuals such as, for instance, Coligan et al., CURRENT PROTOCOLS IN IMMUNOLOGY 1, Chapter 5, 1991.

An alternative method involves screening of peptide libraries for binding partners. Transfected cells expressing recombinant mouse CC-CKR5 are used to identify peptides from a peptide or phosphopeptide library which interact with mouse CC-CKR5. Sequencing of the peptides leads to identification of consensus peptide sequences which might be found in interacting proteins.

Mouse CC-CKR5 binding partners idenitified by any of these methods or other methods, which would be known to those of ordinary skill in the art, as well as those putative binding partners discussed above, cain be used in the assay method of the invention. Assaying for the presence of mouse CC-CKR5/binding partner complex is accomplished by, for example, radioligand bindinig assays and calcium mobilization studies. In the presence of test substances which interrupt or inhibit formation of mouse CC-CKR5/binding partner interaction, a decreased amount of complex will be determined relative to a control lacking the test substance.

Assays for free binding partner are accomplished by radioligand binding assays and calcium mobilization. In the presence of test substances which interrupt or inhibit formation of mouse CC-CKR5/binding partner interaction, an increased amount of binding partner will be determined relative to a control lacking the test substance.

Polypeptides of the invention also can be used to assess human CC-CKR5 binding capacity of mouse CC-CKR5 binding molecules in cells or in membrane preparations.

Agonists and Antagonists—Assays and Molecules

With the discovery of the mouse CC-CKR5 gene, it is now possible to produce mice capable of expressing the human CC-CKR5 receptors. The mouse CC-CKR5 receptor from a mouse strain can be knocked out and replaced with the receptor with the human CC-CKR5 receptor. In a preferred embodiment, the mouse CC-CKR5 gene is replaced with the human HDGNR 10 clone, shown in FIG. 2. For example, a mouse gene knockout strain is created by disrupting the mouse CC-CKR5 gene with a neo gene cassette to knock out the endogenous mouse gene. This strain can then be used to re-insert the human HDGNR10 receptor to replace the loss of the mouse CC-CKR5 receptor. Such strains may be very useful as animal models in the study of T-cell mediated inflammation. In addition, because of the important role of human CC-CKR5 in HIV-1 infection, it is believed that these animals will serve as useful models in the study of this human virus.

Using these gene knockout animals, compounds can be screened to determine their effects on the activity of the human CC-CKR5 receptor. For example, these mice of the present invention may be employed in a screening process for compounds which activate (agonists) or inhibit activation (antagonists) of human CC-CKR5 receptor. In addition, changes in the levels of expression of the human CC-CKR5 receptor in response to a compound can be assess.

In general, such screening procedures involve producing gene knockout mice which express the human receptor polypeptide of the present invention. Mice are then administered a test compound and binding, stimulation or inhibition of a functional response is observed.

Alternatively, screening may be performed in vitro using cells which express the mouse CC-CKR5 receptor on the surface thereof. Such cells include cells from mammals or insects such as Drosophila. In particular, a polynucleotide encoding the receptor of the present invention is employed to transfect cells to thereby express the mouse CC-CKR5. Cells expressing the receptor are then contacted with a test compound to observe binding, stimulation or inhibition of a functional response.

One such screening procedure involves the use of melanophores which are transtfected to express the mouse CC-CKR5 of the present invention. Such a screening technique is described in PCT WO92/01810. In one embodiment, this technique is employed to screen for compounds which inhibit activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor. The technique may also be employed for screening of compounds which activate the receptor by contacting such cells with compounds to be screened and determining whether such compound generates a signal, i.e., activates the receptor.

Other screening techniques include the use of cells which express the mouse CC-CKR5 (for example, transfected CHO cells) in a system which measures extracellular pH changes caused by receptor activation. (See e.g., *Science*, 1989, 246:181–296). In this technique, compounds may be contacted with cells expressing the receptor polypeptide of the present invention. A second messenger response, e.g., signal transduction or pH change, is then measured to determine whether the potential compound activates or inhibits the receptor.

Another screening technique involves introducing RNA encoding the mouse CC-CKR5 into Xenopus oocytes to transiently express the receptor. The receptor oocytes are then contacted with the receptor ligand and a compound to be screened. Inhibition or activation of the receptor is then determined by detection of a signal, Such as, calcium, proton, or other ions, in the case of screening for compounds which are thought to inhibit activation of the receptor.

Another screening technique involves expressing the mouse CC-CKR5 in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antagonists and thus inhibit activation of the CC-CKR5 by determining inhibition of binding of labeled ligand to cells which have the receptor on the surface thereof. Such a method involves transfecting a eukaryotic cell with DNA encoding mouse CC-CKR5 such that the cell expresses the receptor on its surface. The cells are then contacted with a compound in the presence of a labeled form of a known ligand. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand.

Another method involves screening for CC-CKR5 inhibitors by determining inhibition or stimulation of mouse CC-CKR5-mediated cAMP and/or adenylate cyclase accumulation. Such a method involves transfecting a eukaryotic cell with mouse CC-CKR5 receptor to express the receptor on the cell surface. The cell is then exposed to potential antagonists in the presence of mouse CC-CKR5. The amount of cAMP accumulation is then measured. If the potential antagonist binds the receptor, and thus inhibits CC-CKR5 binding, the levels of mouse CC-CKR5-mediated cAMP, or adenylate cyclase, activity will be reduced or increased.

Other methods for detecting agonists and antagonists of the receptor include the yeast based technologies described in U.S. Pat. No. 5,482,835.

The present invention also provides a method for determining whether a ligand not known to be capable of binding to a CC-CKR5 receptor call bind to the receptor. This method comprises contacting a mammalian cell which expresses a mouse CC-CKR5 receptor with the ligand under conditions permitting binding of ligands to the CC-CKR5 receptor, and detecting the presence of a ligand which binds to the mouse receptor thereby determining whether the ligand binds to a CC-CKR5 receptor. The systems hereinabove described for determining agonists and/or antagonists may also be employed for determining ligands which bind to the receptor.

Examples of potential CC-CKR5 receptor antagonists include antibodies or, in some cases, oligopeptides which bind to the receptor but do not elicit a second messenger response such that the activity of the receptor is prevented.

Potential antagonists also include proteins which are closely related to the ligand of the mouse CC-CKR5 receptor, i.e. a fragment of the ligand, which have lost biological function and, when binding to a CC-CKR5 receptor, elicit no response.

A potential antagonist also includes an antisense construct prepared through the use of antisense technology. Antisense technology can be used to control gene expression through triple-helix formation or antisense DNA or RNA, both methods of which are based on biding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 1979, 6:3073; Cooney et al., *Science*, 1988, 241:456; and Dervani et al., *Science*, 1991, 251:1360), thereby preventing transcription and production of the a CC-CKR5 receptor. The antisense RNA oligonucleotide hybridizes to the mRNA in vivo and blocks translation of the mRNA molecule into the CC-CKR5 receptor (antisense—Okano, *J. Neurochem.*, (1991) 56:560; Oligodeoxynucleotides as Antisense Inhibitors of Gene Expression, CRC Press, Boca Raton, Fla. (1988)). The oligonucleotides described above can also be delivered to cells such that the antisense RNA or DNA is expressed in vivo to inhibit production of a CC-CKR5 receptor.

Another potential antagonist is a small molecule which binds to the mouse CC-CKR5 receptor, making it inaccessible to ligands such that normal biological activity is prevented. Examples of small molecules include, but are not limited to, small peptides or peptide-like molecules.

Potential antagonists also include soluble forms of the mouse CC-CKR5 receptors e.g. fragments of the receptor, which bind to the ligand and prevent the ligand from interacting with membrane bound CC-CKR5 receptors.

CC-CKR5 receptors are ubiquitous in the mammalian host and are responsible for many biological functions, including many pathologies. Accordingly, it is desirous to find compounds and drugs which stimulate CC-CKR5 on the one hand and which can inhibit the function of CC-CKR5 on the other hand.

Agonists and antagonists for a CC-CKR5 receptor are employed for therapeutic and prophylactic purposes in mediating T cell mediated inflammatory processes, and in particular, the inhibition of HIV-1 infection, among others.

This invention additionally provides a method of treating an abnormal condition related to all excess of CC-CKR5 activity which comprises administering to a subject an inhibitor compound (antagonist) as hereinabove described along with a pharmaceutically acceptable carrier in an amount effective to inhibit activation by blocking binding of ligands to the CC-CKR5 receptor, or by inhibiting, a second signal, and thereby alleviating the abnormal condition.

The invention also provides a method of treating abnormal conditions related to an under-expression of CC-CKR5 and its activity, which comprises administering to a subject a therapeutically effective amount of a compound which activates the receptor polypeptide of the present invention (agonist) as described above, in combination with a pharmaceutically acceptable carrier, to thereby alleviate the abnormal condition.

Compositions and Kits

Compounds which activate or inhibit such receptor, may be employed in combination with a suitable pharmaceutical carrier. Such compositions comprise a therapeutically effective amount of the polypeptide or compound, and a pharmaceutically acceptable carrier or excipient. Such carriers include but are not limited to, saline, buffered saline, dextrose, water glycerol, ethanol, and combinations thereof. The formulation should suit the mode of administration. Selection of an appropriate carrier in accordance with the mode of administration is routinely performed by those skilled in the art.

The invention further relates to pharmaceutical packs and kits comprising one or more containers filled with one or more of the ingredients of the aforementioned compositions of the invention.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes, among others.

The pharmaceutical compositions generally are administered in an amount effective for treatment or prophylaxis of a specific indication or indications. In general, the compositions are administered in an amount of at least about 10 $\mu$g/kg body weight. In most eases they will be administered in an amount not in excess of about 8 mg/kg body weight per day. Preferably, in most cases, the administered dose is from about 10 $\mu$g/kg to about 1 mg/kg body weight, daily. It will be appreciated that optimum dosage will be determined by standard methods for each treatment modality and indication, taking into account the indication, its severity, route of administration, complicating conditions and the like.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples are carried out using standard techniques, which are well known and routine to those of skill in the art, except where otherwise described in detail. Routine molecular biology techniques of the following examples can be carried out as described in standard laboratory manuals, such as Sambrook et al.

Example 1

Expression of Murine CC-CKR5 Using Human Embryonic Kidney Cells 293

The DNA sequence encoding murine CC-CKR5 in the deposited polynucleotide is amplified using PCR oligonucleotide primers specific to the amino and carboxy terminal sequences of the murine CC-CKR5 gene. Additional nucleotides containing restriction sites to facilitate cloning are added to the 5' and 3' sequences, respectively.

The 5' oligonucleotide primer has the sequence: 5'-AGGCCTAAGCTTTGCGGATGGATTTTCAAGGGTCAG-3' (SEQ ID NO:4) containing recognition sequences for StuI and HindIII (underlined in primer sequence) followed by 20-bases of the murine CC-CKR5 gene. The 3' oligonucleotide primer has the sequence: 5'-CTCGAGGATCCTATCATAAACCAGTAGAAACTTC-3' (SEQ ID NO:5) containing the recognition sequences for XhoI and BamHI (underlined in primer sequence) followed by 21 bases of the murine CC-CKR5 gene. The region of the CC-CKR5 gene amplified by these primers in underlined in FIG. 1.

Using standard PCR reaction conditions, a 1084 base pair fragment was generated from a reaction that contained the 5' and 3' primers and as the PCR template the CC-CKR5 gene cloned into pBluescript. The PCR product was extracted with phenol-chloroform, precipitated with ethanol and then digested with HindIII and BamHI. The digested CC-CKR5 fragment was gel purified using a QIAGEN QIAEX DNA fragment purification kit. This fragment was cloned into plasmid pCDN using the unique Hind III and BamHI sites. pCDN contains: (1) an *E. coli* origin of replication effective for propagation in *E. coli* and other procaryotic cells; (2) an ampicillin resistance gene for selection of plasmid-containing procaryotic cells; (3) a CMV promoter, a polylinker, and a polyadenylation site; (4) an SV40 origin of replication for propagation in eukaryotic cells; (5) a gene encoding murine dihydrofolate reductase for selection of cells transformed with the plasmid such that these cells are able to grow in the absence of nucleosides; and (6) a gene encoding resistance to geneticin for selection of transformed cells. The fragment was cloned into the polylinker site such that expression of the murine CC-CKR5 receptor was directed by the CMV promoter. The ligation mixture was transformed into *E. coli* strain DH5α and transformed colonies selected by growth in the presence of ampicillin. Recombinant plasmids containing the murine CC-CKR5 fragment were identified by restriction analysis using HindIII and BamHI. The CC-CKR5 fragment from three individual clones were analyzed by DNA sequencing to ensure that no base changes were introduced during the PCR amplification.

For expression of the murine CC-CKR5 receptor, human embryonic kidney cells 293 were transfected with the pCDNmCC-CKR5 by lipofectamine (GIBCO-Life Sciences) in accordance with the manufacturer's instructions. Stable cell lines were obtained by selection with geneticin. Expression of the murine CC-CKR5 was detected by radiolabeled binding assays using $^{125}$I-RANTES. Competition binding studies were performed again using $^{125}$I-RANTES and commercially available chemokines such as MIP-1α, MIP-1β, MCP-1, -2, -3 and eotaxin.

Example 2

Production of Gene Knockotut Mice

A targeting vector for creating a gene knockout mouse is constructed using a 2.2 kb genomic fragment including 0.55 kb upstream of the translation initiation codon and 1.65 kb downstream of the initiation codon. The fragment was isolated from a 129SVJ mouse genomic library. A fragment containing a gene that confers resistance to neomycin is inserted into a unique EcoRV site which is 200 bp downstream of the translation initiation codon and a herpes simplex virus thymidine kinase cassette is ligated to the 5' end of the genomic fragment. ES D3 cells are transfected with linearized vector. Transfected clones are isolated by selection in 2 μM gancyclovir and 175 μg/ml of G418. Positive ES cells are identified by Southern blot hybridization using the neomycin resistance gene as a probe. The ES cell clones containing the disrupted CC-CKR5 locus are microinjected into Balb/c blastocysts to generate germ-linie chimera, then bred to Balb/c females to produce heterozygous mice. Heterozygous mice are bred to obtain the homozygous knock-out mice.

What is claimed is:

1. An isolated polypeptide comprising an amino acid sequence as set forth in SEQ ID NO:2.

2. An isolated polypeptide consisting of the amino acid sequence set forth in SEQ ID NO:2.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 2440
      (B) TYPE: Nucleic Acid
      (C) STRANDEDNESS: Single
      (D) TOPOLOGY: Linear (iv) ANTI-SENSE: No (xi) SEQUENCE DESCRIPTION: SEQ ID NO: 1:

```
GAGAGAGAGA GAGAGAGAGA GaGaGaGAGA GAGAGAGAGA GAGAGAGaGA            50
```

-continued

| | |
|---|---|
| GAGAGAGAGA GAGAGAGAGA GAGAGAGAGA GAGAGAGAGA TCTTATTAGT | 100 |
| TACCAAGGAG TGACAAGCAA CATGTCAGTT AAGGTTTCAT ACTGCCCAAA | 150 |
| TTCAAAGTAA GTTACTTCCT GGTGGTGTGG TTTTTATATT AACATTCATT | 200 |
| CTCTCTATAC TTGGGGAGTG TTTTATCCAG AAAAACATAA ACAGTATATT | 250 |
| GCTTGCCTCA AGCAGTTAAc TCAAGTGTTT AGCAAAtGCA TATGTAATAC | 300 |
| TATAGAACAG TAATTAGCAC CCACTACTCA TTCTTTCTGG CATTTGTGTG | 350 |
| AACTCTAGGA TTTATGGATA AATGCCTAGA AGCAGCATCT TCAATAGAGA | 400 |
| TCTTAAGCCC ATGAATTATA TAGGACCTGA CTCAGTTTCA CAGATTAATT | 450 |
| CACCCCACAT TGATATGGAA AGCAAAATTT TATTTGATCA AATGCATCTT | 500 |
| TGGTGAATTT CGAGCCATCT GATGATGGGA AAATTAAATG TAGAAGTCTA | 550 |
| TGCCTCAAAG ACCTACTAAG TTATAAAACA ATAATTGTGG TAGGCCAGCA | 600 |
| ATTGCTTTAA CCTTTATTAA GCATTGTCTT TTATTTATTC ATAGGCTCTT | 650 |
| GCAGGATGGA TTTTCAAGGG TCAGTTCCGA CCTATATCTA TGACATCGAT | 700 |
| TAtGGTATGT CAGCACCCTG CCAAAAAATC AATGtGAAAC AAATTGCAGC | 750 |
| TcAGCTCCtg CCCCCAcTAT ACTCCctGGT ATTCATCTtt GGTTTtGcGG | 800 |
| GAAACATGAT GGTcTTCCTC ATCTTGATAA GCTGCAAAAA GCTGAAGAGC | 850 |
| GTGACTGATA TCTATCTGCT CAACTTGGCC ATCTCtGACC TGcTCTTCCT | 900 |
| GCTCACACTA CCATTCTGGG CTCACTATGC TGCAAATGAG TGGATCTTTG | 950 |
| GGAATATAAT GTGTAAAGTA TTCACAGGTG TCTATCATAT TGGTTATTTT | 1000 |
| GGTGGAATCT TCTTCATTAT CCTCCTGACA ATTGATAGGT ACTTGGCTAT | 1050 |
| TGTCCATGCT GTGTtTGCTT TAAAAGTCAC AACGGTCAAC TTTGGGGTGA | 1100 |
| TAACAAgTGT AGTCACTTGG GTGGTGGCTG TGTTTGCCTC TCTCCCAgAA | 1150 |
| ATAATCTtTA CCAgATCTCA gAAAgAAGGT TtTCATTATA CATGCAGTCC | 1200 |
| TCATTTTCCA CACACTCAGT ATCATTTCTG GAAGAGTTTC CAAACATTAA | 1250 |
| AGATGGTCAT CTTGAGCCTG ATCCTGCCTC TACTTGTCAT GATCATCTGC | 1300 |
| TACTCAGGAA TTCTCCACAC CCTGTTTCGC TGTAGGAATG AGAAGAAGAG | 1350 |
| GCACAGGGCT GTGAGGCTCA TCTTTGCCAT CATGATTGTC TACTTTCTCT | 1400 |
| TCTGGACTCC CTACAACATT GTCCTCCTCC TGACCACCTT CCAGGAATTC | 1450 |
| TTTGGACTGA ATAACTGCAG TAGTTCTAAT AGACTAGACC AGGCCATGCA | 1500 |
| GGCAACAGAG ACTCTTGGAA TGACACACTG CTGCCTAAAC CCTGTCATCT | 1550 |
| ATGCCTTTGT TGGAGAgAAG TTCCGGAGTT ATCTCTCAGT GTTCTTCCGA | 1600 |
| AAACACATTG TCAAACGCTT TTGCAAACGG TGTTCAATTT TCCAGCAAGA | 1650 |
| CAATCCTGAT CGTGTAAGCT CAGTCTATAC CCGATCCACA GGAGAACATG | 1700 |
| AAGTTTCTAC TGGTTTATGA CCTGGTTGAC TTTTGTGTAT CACGTAGTTT | 1750 |
| TTCTATGCAG CTTGGGAGTA GGAATGGTTC TTTTAAAAAA GAAATTAGTA | 1800 |
| TCATAGAGGG CCCAAGATAC ATGCATCTTT TTGATATTTA TTTTTAGATA | 1850 |
| GATTGGATCT TTTAAAACTG AATGGGGAGG TTGGGGTGGG GGAGCAgGGA | 1900 |
| gAACGAgTCT TTTATCAGGG CCGGGAAATA TGCACAAAGA gACTTGAGTC | 1950 |
| AGGTGCCATG ACCCATATGC AAAGGGACGG ACACAGGGCC gATGCTGTTG | 2000 |
| CCTAgAAATG ACGTGTCTCC CCGCTGGGTT CCTGAAAGGC GGCTGTAAAT | 2050 |

```
ATGCCTGATT GCCATAAAGT CGCTTCTTGC TGTCTATGGA TGTGCCTGAC          2100

TGCCAACAGG GAAGAACCAC TTCTGCATAT AAAATGTAGA GTCAGCAGAA          2150

CTTGGGGTAA ATTGAAGTTA GAGGTGCATA AGAACCCCTA GGCTTAGTTA          2200

GGTTGAAATA CCCATTGAGG AAACAGCAAA TACAAAGGAA GAATAAAGAG          2250

TTTAGCCGGG AAGGTAGTCT CATTTTACAG CCGGAATATA ATGTTATCTC          2300

AGGCTAGCAT TTTGTTCCTG CCTTCAGACC TAAATCCTAC CACACCGGGA          2350

CTGTGAAACA CCTGGATTAT GAATCATGAg CCTGAgGTCT AgGAATAATA          2400

ACGTTTGTgA TTTTAgATgA GGGCTGTTTA CATAgTTTGA                     2440
```

(2) INFORMATION FOR SEQ ID NO:2:

(i) SEQUENCE CHARACTERISTICS:
        (A) LENGTH: 354
        (B) TYPE: Amino Acid
        (D) TOPOLOGY: Linear (xi) SEQUENCE DESCRIPTION: SEQ ID NO: 2:

```
Met Asp Phe Gln Gly Ser Val Pro Thr Tyr Ile Tyr Asp Ile Asp
                 5                  10                  15

Tyr Gly Met Ser Ala Pro Cys Gln Lys Ile Asn Val Lys Gln Ile
                20                  25                  30

Ala Ala Gln Leu Leu Pro Pro Leu Tyr Ser Leu Val Phe Ile Phe
                35                  40                  45

Gly Phe Ala Gly Asn Met Met Val Phe Leu Ile Leu Ile Ser Cys
                50                  55                  60

Lys Lys Leu Lys Ser Val Thr Asp Ile Tyr Leu Leu Asn Leu Ala
                65                  70                  75

Ile Ser Asp Leu Leu Phe Leu Leu Thr Leu Pro Phe Trp Ala His
                80                  85                  90

Tyr Ala Ala Asn Glu Trp Ile Phe Gly Asn Ile Met Cys Lys Val
                95                 100                 105

Phe Thr Gly Val Tyr His Ile Gly Tyr Phe Gly Gly Ile Phe Phe
               110                 115                 120

Ile Ile Leu Leu Thr Ile Asp Arg Tyr Leu Ala Ile Val His Ala
               125                 130                 135

Val Phe Ala Leu Lys Val Thr Thr Val Asn Phe Gly Val Ile Thr
               140                 145                 150

Ser Val Val Thr Trp Val Val Ala Val Phe Ala Ser Leu Pro Glu
               155                 160                 165

Ile Ile Phe Thr Arg Ser Gln Lys Glu Gly Phe His Tyr Thr Cys
               170                 175                 180

Ser Pro His Phe Pro His Thr Gln Tyr His Phe Trp Lys Ser Phe
               185                 190                 195

Gln Thr Leu Lys Met Val Ile Leu Ser Leu Ile Leu Pro Leu Leu
               200                 205                 210

Val Met Ile Ile Cys Tyr Ser Gly Ile Leu His Thr Leu Phe Arg
               215                 220                 225

Cys Arg Asn Glu Lys Lys Arg His Arg Ala Val Arg Leu Ile Phe
               230                 235                 240

Ala Ile Met Ile Val Tyr Phe Leu Phe Trp Thr Pro Tyr Asn Ile
               245                 250                 255

Val Leu Leu Leu Thr Thr Phe Gln Glu Phe Phe Gly Leu Asn Asn
```

```
                260                 265                 270
Cys Ser Ser Ser Asn Arg Leu Asp Gln Ala Met Gln Ala Thr Glu
            275                 280                 285
Thr Leu Gly Met Thr His Cys Cys Leu Asn Pro Val Ile Tyr Ala
            290                 295                 300
Phe Val Gly Glu Lys Phe Arg Ser Tyr Leu Ser Val Phe Phe Arg
            305                 310                 315
Lys His Ile Val Lys Arg Phe Cys Lys Arg Cys Ser Ile Phe Gln
            320                 325                 330
Gln Asp Asn Pro Asp Arg Val Ser Ser Val Tyr Thr Arg Ser Thr
            335                 340                 345
Gly Glu His Glu Val Ser Thr Gly Leu
            350
```

(2) INFORMATION FOR SEQ ID NO:3:

(i) SEQUENCE CHARACTERISTICS:
        (A) LENGTH: 1059
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 3:

```
ATGGATTATC AAGTGTCAAG TCCAATCTAT GACATCAATT ATTATACATC            50

GGAGCCCTGC CAAAAAATCA ATGTGAAGCA AATCGCAGcC CGCCTCCTGC           100

CTCCGCTCTA CTCACTGGTG TTCATCTTTG GTTTtGTGGG CAACATGCTG           150

GTCATCCTCA TCCTGATAAA CTGcAAAAGG CTGAAGAGCA TGACTGACAT           200

CTaCCTGCTC AACCTGGCCA TCTCTGACCT GTTTTTCCTT CTTACTGTCC           250

CCTTCTGGGC TCACTATGCT GCCGCCCAGT GGGACTTTGG AAATACAATG           300

TGTCAACTCT TGACAGGGCT CTATTTTATA GGCTTCTTCT CTGGAATCTT           350

CTTCATCATC CTCCTGACAA TCGATAGGTA CCTGGCTGTC GTCCATGCTG           400

TGTTTGCTTT AAAAGCCAGG ACGGTCACCT TTGGGGTGGT GACAAGTGTG           450

ATCACTTGGG TGGTGgCTGT GTTTGCGTCT CTCCCAGGAA TCATCTTTAC           500

CAGATCTCAA AAAGAAGGTC TTCATTACAC CTGCAGCTCT CATTTTCCAT           550

ACAGTCAGTA TCAATTCTGG AAGAATTTCC AGACATTAAA GATAGTCATC           600

TTGGGGCTGG TCCTgCCgCT GCTTGTCATG GTCATCTGCT ACTCGGGAAT           650

CCTAAAAACT CTGCTTCGGT GTCGAAATGA AAGAAGAGG CACAGGGCTG            700

TGAGGCTTAT CTTCACCATC ATGATTGTTT ATTTTCTCTT CTGGGCTCCC           750

TACAACAtTG TCCTTCTCCT GAACACCTTC CAGGAATTCT TTGGCCTGAA           800

TAATTGCAGT AGCTCTAACA GGTTGGACCA AGCTATGCAG GTGACAGAGA           850

CTCTTGGGAT GACGCACTGC TGCATCAACC CCATCATCTA TGCCTTTGTC           900

GGGGAGAAGT TCAGAAACTA CCTCTTAGTC TTCTTCCAAA AGCACATTGC           950

CAAACGCTTC TgCAAATGCT GTTCTATTTT CCAGCAAGAG GCTCCCGAGC          1000

GAGCAAGCTC AGTTTACACC CGATCCACTG ggGAGCAGGA AATATCTGTG          1050

GGCtTGTGA                                                       1059
```

```
(2) INFORMATION FOR SEQ ID NO:4:

(i) SEQUENCE CHARACTERISTICS:
        (A) LENGTH:  36
        (B) TYPE:  Nucleic Acid
        (C) STRANDEDNESS:  Single
        (D) TOPOLOGY:  Linear (iv) ANTI-SENSE:  No (xi) SEQUENCE DESCRIPTION:  SEQ ID NO: 4:

AGGCCTAAGC TTTGCGGATG GATTTTCAAG GGTCAG                                      36

(2) INFORMATION FOR SEQ ID NO:5:

(i) SEQUENCE CHARACTERISTICS:
        (A) LENGTH:  34
        (B) TYPE:  Nucleic Acid
        (C) STRANDEDNESS:  Single
        (D) TOPOLOGY:  Linear (iv) ANTI-SENSE:  No (xi) SEQUENCE DESCRIPTION:  SEQ ID NO: 5:

CTCGAGGATC CTATCATAAA CCAGTAGAAA CTTC                                        34
```